United States Patent [19]

Mizushima et al.

[11] Patent Number: 4,849,451
[45] Date of Patent: Jul. 18, 1989

[54] FAT EMULSION CONTAINING PROSTAGLANDIN

[75] Inventors: Yutaka Mizushima, Kawasaki; Hironaka Aihara, Kitamoto; Susumu Otomo, Konosu; Kazumasa Yokoyama, Toyonaka; Hiroyuki Okamoto, Akashi; Tadakazu Suyama, Kyoto, all of Japan

[73] Assignees: Taisho Pharmaceutical Co., Ltd., Tokyo; The Green Cross Corporation, Osaka, both of Japan

[21] Appl. No.: 865,647

[22] Filed: May 16, 1986

Related U.S. Application Data

[63] Continuation of Ser. No. 610,412, May 15, 1984, abandoned.

[30] Foreign Application Priority Data

May 20, 1983 [JP] Japan ................................. 58-88760

[51] Int. Cl.[4] ............................................ A61K 31/215
[52] U.S. Cl. ..................................................... 514/530
[58] Field of Search ......................................... 514/530

[56] References Cited

U.S. PATENT DOCUMENTS

| 3,927,213 | 12/1975 | Lippmann | 514/163 |
| 4,153,727 | 5/1979 | Matsui et al. | 514/573 |
| 4,340,594 | 7/1982 | Mizushima et al. | 514/179 |
| 4,443,473 | 4/1984 | Buckwalter | 514/487 |

OTHER PUBLICATIONS

Remington's Pharmaceutical Sciences, 16th ed., Mack Publishing Company, pp. 1453-1457 (1980).
The Merck Index, 10th Ed., Windholz, Eds., published by Merck & Co., Inc. Rahway, N.J., 1983, 2181, "Cholesterol", p. 312.

Primary Examiner—Douglas W. Robinson
Assistant Examiner—J. Kilcoyne
Attorney, Agent, or Firm—Cushman, Darby & Cushman

[57] ABSTRACT

A fat emulsion containing a prostaglandin $E_1$ alkyl ester represented by the general formula

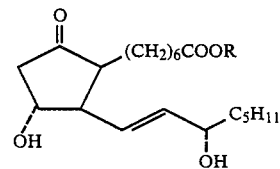

wherein R denotes an alkyl group having 1 to 30 carbon atoms.

The fat emulsion can be administered intravenously, has a long half-life of its effective ingredient, prostaglandin $E_1$ alkyl ester, in the living body as well as a focus selectivity.

8 Claims, 1 Drawing Sheet

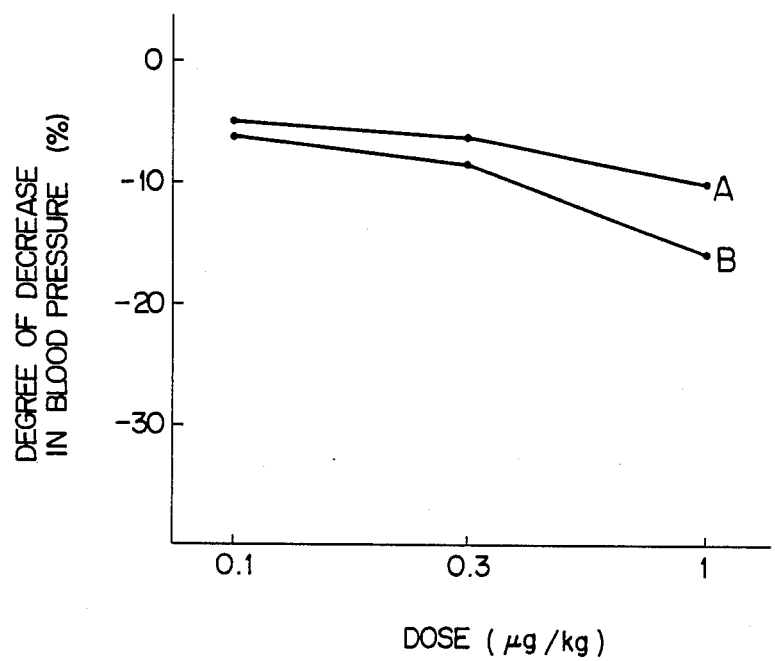

FAT EMULSION CONTAINING PROSTAGLANDIN

This is a continuation of application Ser. No. 610,412, filed May 15, 1984, which was abandoned upon the filing hereof.

This invention relates to a fat emulsion containing prostaglandin. More particularly, it relates to a fat emulsion containing prostaglandin $E_1$ alkyl ester.

Prostaglandins (hereinafter referred to briefly as PGs) have diversified physiological actions including vasodilative action, improvement of peripheral blood circulation, hypotensive action, antilipolysis and natriuresis, and hence their application to pharmaceuticals have been investigated for some time past.

However, when the potentially useful PGs are applied as pharmaceuticals, there emerge the problems that (1) they are readily transformed metabolically into inactive substances in living bodies and (2) they exhibit an unsatisfactory focus selectivity. As the result, the PGs preparations in general have drawbacks in that they require frequent administration and thus give greater pain to the patients and moreover their actions to other tissues than aimed at manifest themselves as side effects.

The inventors made extensive studies on pharmaceutical application of PGs to overcome the above difficulties and found previously that a preparation made by the inclusion of $PGE_1$ in a fat emulsion for intravenous administration permits of intravenous administration accompanied with reduced manifestation of side effects [Japanese Patent Application Kokai (Laid-open) No. 222014/83]. On further study the inventors have succeeded, by the inclusion of $PGE_1$ alkyl ester (hereinafter referred to briefly as $PGE_1E$) in the fat emulsion, in developing a preparation which has a prolonged half-life of PGs in living body as well as a satisfactory focus selectivity, and thus accomplished this invention.

$PGE_1E$ is more liposoluble than $PGE_1$ and hence a larger amount of it can be incorporated into the fat emulsion, so that a higher activity can be expected of its fat emulsion even in a smaller dose than that of a fat emulsion containing $PGE_1$.

An object of this invention is to provide a $PGE_1E$ fat emulsion for intravenous administration which releases its effective ingredient sustainedly and at the same time has a good focus selectivity.

Other objects and advantages of this invention will become apparent from the following description.

The accompanying drawing shows the degree of decrease in blood pressure observed when the preparation of this invention or a control preparation is separately administered intravenously. In the drawing, line B indicates the degree of decrease in blood pressure of the preparation of this invention and line A indicates that of the control preparation.

In this invention, $PGE_1E$ refers to a compound represented by the general formula

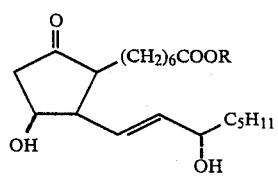

wherein R denotes an alkyl group having 1 to 30 carbon atoms.

The alkyl group in the above general formula may be of either straight chain or branched chain. The number of its carbon atoms is 1 to 30, preferably 1 to 15 and more preferably 3 to 10. Examples of such alkyl groups include methyl, ethyl, n-propyl, isopropyl, n-butyl, isobutyl, tert-butyl, n-pentyl, n-hexyl, n-heptyl, n-octyl, n-nonyl and n-decyl.

The $PGE_1E$ content of the present fat emulsion can be suitably varied according to the composition and use of the emulsion, but it should cover the effective amount which is in the range of 100 to 0.2 μg/ml.

The fat emulsion, as herein referred to, comprises, as main constituents, 5-50% (W/V) of soybean oil, 1-50, preferably 5-30, parts by weight of a phospholipid for 100 parts by weight of the soybean oil, and a proper quantity of water. In addition, the fat emulsion may contain, if necessary, emulsifying adjuvant [for example, 0.01-0.3% (W/V) of a fatty acid having 6-22, preferably 12-20, carbon atoms or a physiologically acceptable salt thereof], stabilizers [for example, 0.001-0.5, preferably 0.005-0.1, %(W/V) of cholesterol or 0.01-5, preferably 0.05-1, %(W/V) of phosphatidic acid], high-molecular-weight stabilizing adjuvant [for example, 0.1-5, preferably 0.5-1, parts by weight of albumin, dextran, vinyl polymers, nonionic surface active agents, gelatin, or hydroxyethylstarch for 1 part by weight of $PGE_1E$], or isotonizing agents (for example, glycerol or glucose in an amount required for the isotonization).

The soybean oil for use in the present emulsion is a highly purified soybean oil, preferably that one (purity: 99.9% or above in terms of total glyceride including tri-, di-, and mono-glyceride) obtained by further purifying common refined soybean oil by steam distillation.

The phospholipid, as herein referred to, is a purified phopsholipid such as egg yolk phospholipid or soybean phospholipid, which is obtained by the common fractionation technique using an organic solvent. For instance, it is prepared by slowly adding, with stirring, acetone to a crude yolk phospholipid dissolved in a cold n-hexane-acetone mixture, collecting the insolubles by filtration, repeating the procedure of dissolution followed by precipitation, and finally removing the solvent by distillation. The product comprises phosphatidylcholine and phosphatidylethanolamine as major constituents and minor amounts of other phospholipids such as phosphatidylinositol, phosphatidylserine, and sphingomyelin. Various phospholipids can be used each alone or in combinations.

The fatty acids of 6-22 carbon atoms for use as emulsifying adjuvant are those suitable for use in pharmaceuticals. They may be of either straight chain or branched chain. Most preferred are straight chain fatty acids such as stearic, oleic, linolic, palmitic, linolenic, and myristic acids. The salts should be physiologically acceptable ones such as, for example, salts with alkali metals such as sodium and potassium or with alkaline earth metals such as calcium.

The cholesterol and the phosphatidic acid for use as a stabilizer are those which are suitable for use in pharmaceuticals.

Suitable high-molecular-weight substances for use as stabilizing adjuvant are as follows: The albumin should be of the human origin, in view of the problem of antigenicity. Suitable vinyl polymers include polyvinylpyrrolidone.

Suitable nonionic surface active agents are polyalkylene glycols (for example, polyethylene glycol having an average molecular weight of 1,000–10,000, preferably 4,000–6,000), polyoxyalkylene copolymers (for example, a polyoxyethylene-polyoxypropylene copolymer having an average molecular weight of 1,000–20,000, preferably 6,000–10,000), polyoxyalkylene derivatives of hardened castor oil [for example, hardened castor oil polyoxyethylene-(40), or -(20), or -(100) ether], and polyoxyalkylene derivatives of castor oil [for example, castor oil polyoxyethylene-(20), or -(40), or -(100) ether].

The present fat emulsion is produced, for example, in the following manner: Predetermined amounts of $PGE_1E$, phospholipid, and, if necessary, the aforementioned additives are mixed with soybean oil and the mixture is heated at 40° to 75° C. to accelerate dissolution, whereby a homogeneous solution is formed. The solution is mixed with a necessary quantity of water and emulsified at 20° to 80° C. by means of a common mixer (e.g. a homomixer) to form a coarse emulsion. A stabilizer and an isotonizing agent may be added at this stage. The coarse emulsion is then subjected to size diminution treatment at 20° to 80° C. by using a homogenizer (e.g. a homogenizer of the high pressure-jet type such as Manton-Gaulin homogenizer or of the ultrasonic type), resulting in a homogenized, finely dispersed fat emulsion containing $PGE_1E$. This emulsion has an excellent storage stability and the average particle size is $1.0\mu$ or below. The homogenization of a coarse emulsion by means of Manton-Gaulin homogenizer is carried out by passing the coarse emulsion 1 to 2 times through the homogenizer under a first-stage pressure of 100–150 $kg/cm^2$ and then 5 to 15 times under a second stage pressure of 400–700 $kg/cm^2$.

The present fat emulsion is administered through a parenteral route, preferably intravenously. For instance, a dose of 1 to 100 $\mu g$ in terms of $PGE_1$ is administered once a day by the continuous intravenous infusion at a rate of 0.02–0.2 ng/kg body weight per minute.

Since the fat emulsion of this invention has a strong medicinal action, focus selectivity, and is of sustained release it permits effective treatment of the patient with a small dose.

Further, the present emulsion does not undergo inactivation which is liable to occur with conventional PG preparations such as an $\alpha$-cyclodextrin clathrate compound of PG. As a consequence, it has become possible to administrate the present emulsion by intravenous injection which was believed to be impossible with conventional PG preparations. The present emulsion exhibits a steady medicinal effect with a small dose, resulting in reduced side effects. In addition, there is observed none of those swelling, dull pain, redness, and fever which are apt to occur in the region where a conventional PG preparation was introduced.

This invention is illustrated below in detail with reference to Test Examples and Examples of the fat emulsion of this invention, but the invention is not limited thereto.

TEST EXAMPLE 1

A group of 4–6 male adult mongrel dogs each weighing about 10 kg was used in each test. The dog was anesthetized with sodium pentobarbital (35 mg/kg, intravenous injection). Sixty minutes after the anesthesia, the blood pressure (mmHg) was measured. After additional 30 minutes, the present fat emulsion prepared as in Example 2 described hereinafter or a control preparation prepared by dissolving $PGE_1$ methyl ester in physiological saline was administered intravenously in a dose of 0.1, 0.3 and 1 $\mu g/kg$ in terms of $PGE_1$ to respective dog groups, and examined for its effect on the blood pressure of the dogs.

The results were as shown in FIG. 1. As is apparent from FIG. 1, the hypotensive action of the preparation of this invention is distinctly stronger than that of the control preparation.

TEST EXAMPLE 2

The $LD_{50}$ value in intravenous administration of the present preparation prepared as in Example 2 described hereinafter was 200 ml or more/kg body weight for 10% fat emulsion and 150 ml or more/kg body weight for 20% fat emulsion. No hemolyzation was observed at all when the intravenous drip was conducted at a normal rate.

EXAMPLE 1

To 30 g of purified soybean oil, were added 3.6 g of yolk phospholipid, 900 $\mu g$ of $PGE_1$ propyl ester, 0.15 g of sodium palmitate, and 0.15 g of phosphatidic acid. The mixture was heated at 45° to 65° C. to form a solution. To the solution, was added 200 ml of distilled water, followed by 7.5 g of glycerol of the official grade (Pharmacopoeia of Japan). The mixture was made up to 300 ml with distilled water for injection at 20°–40° C., and coarsely emulsified in "Homomixer". The coarse emulsion was homogenized by passing 10 times through a Manton-Gaulin-type homogenizer under a first-stage pressure of 120 $kg/cm^2$ and a total pressure of 500 $kg/cm^2$. There was obtained a homogenized, finely dispersed fat emulsion containing $PGE_1$ propyl ester. The emulsion, $0.2$–$0.4\mu$ in average size of dispersed droplets, contained none of the droplets of $1\mu$ or above in size.

EXAMPLE 2

To 35 g of purified soybean oil, were added 3.0 g of soybean phospholipid, 850 $\mu g$ of $PGE_1$ methyl ester, 0.10 g of sodium linolate and 0.15 g of phosphatidic acid. The mixture was heated at 40° to 60° C. to form a solution. To the solution, was added 200 ml of distilled water, followed by 7.5 g of glycerol of the official grade (Pharmacopoeia of Japan). The mixture was made up to 300 ml with distilled water for injection at 20° to 40° C., and coarsely emulsified in "Homomixer".

The coarse emulsion was homogenized by passing 10 times through a Manton-Gaulin-type homogenizer under a first-stage pressure of 120 $kg/cm^2$ and a total pressure of 500 $kg/cm^2$. There was obtained a homogenized, finely dispersed fat emulsion containing $PGE_1$ methyl ester. The emulsion, 0.2 to $0.4\mu$ in average size of dispersed droplets, contained none of the droplets of $1\mu$ or above in size.

EXAMPLE 3

To 25 g of purified soybean oil, were added 4.0 g of yolk phospholipid, 800 $\mu g$ of $PGE_1$ ethyl ester, 0.20 g of sodium stearate and 0.20 g of cholesterol. The mixture was heated at 50° to 65° C. to form a solution. To the solution, was added 200 ml of distilled water, followed by 7.5 g of glycerol of the official grade (Pharmacopoeia of Japan). The mixture was made up to 300 ml with distilled water for injection at 20° to 40° C., and coarsely emulsified in "Homomixer". The coarse emulsion was homogenized by passing 10 times through a Manton-Gaulin-type homogenizer under a first-stage pressure of 120 kg/cm$^2$ and a total pressure of 500 kg/cm$^2$.

There was obtained a homogenized, finely dispersed fat emulsion containing PGE$_1$ ethyl ester. The emulsion, 0.2 to 0.4μ in average size of dispersed droplets, contained none of the droplets of 1μ or above in size.

What is claimed is:

1. A fat emulsion for intravenous administration containing prostaglandin E$_1$ alkyl ester comprising 0.2 to 100 μg/ml of a prostaglandin E$_1$ alkyl ester represented by the formula

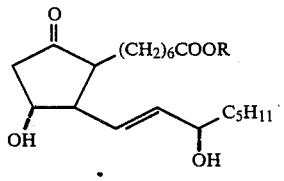

where R denotes an alkyl group selected from the group consisting of methyl, ethyl, n-propyl, iso-propyl, n-butyl, iso-butyl, tert-butyl, n-pentyl, n-hexyl, n-octyl, n-nonyl, and n-decyl, 5–50% (w/v) of soybean oil, 1–50 parts by weight of egg yolk phospholipid or soybean phospholipid per 100 parts by weight of the soybean oil, and a proper quantity of water to make said emulsion.

2. A fat emulsion according to claim 1, which contains as emulsifying adjuvant 0.01–0.3% (w/v) of stearic, oleic, linolic, palmitic, linoleic, or myristic acid, or a physiologically acceptable salt thereof.

3. A fat emulsion according to claim 1, which contains as stabilizer 0.001–0.5% (W/V) of cholesterol or 0.01–5% (W/V) of phosphatidic acid.

4. A fat emulsion according to claim 1, which contains glucose or glycerol as an isotonizing agent.

5. A method for producing a fat emulsion for intravenous administration containing prostaglandin E$_1$ alkyl ester comprising 0.2–100 μg/ml of a prostaglandin E$_1$ alkyl ester represented by the formula

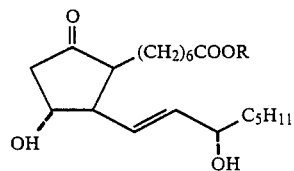

wherein R denotes an alkyl group selected from the group consisting of methyl, ethyl, n-propyl, isopropyl, n-butyl, iso-butyl, tert-butyl, n-pentyl, n-hexyl, n-octyl, n-nonyl and n-decyl 5–50% (w/v) of soybean oil, 1–50 parts by weight of egg yolk phospholipid or soybean phospholipid per 100 parts by weight of the soybean oil, and a proper quantity of water to make said emulsion, which comprises (1) dissolving the prostaglandin E$_1$ alkyl ester and the phospholipid with the soybean oil at 40–75° C. to form a homogeneous solution, (2) mixing the solution with the proper quantity of water at 20–80° C. by means of a mixer to form a coarse emulsion, and (3) homogenizing by passing the coarse emulsion through a high pressure jet-type homogenizer 1–2 times under a first-stage of 100–150 kg/cm$^2$ and then 5–15 times under a second-stage pressure of 400–700 kg/cm$^2$, at 20°–80° C.

6. A method according to claim 5, wherein 0.01–0.3% (w/v) of stearic, oleic, linolic, palmitic, linoleic, or myristic acid, or a physiologically acceptable salt thereof is added as emulsifying adjuvant in the dissolution step.

7. A method according to claim 5, wherein 0.001–0.5%(W/V) of cholesterol or 0.01–5% (W/V) of phosphatidic acid is added as stabilizer of fat emulsion in the dissolution step.

8. A method according to claim 5, wherein glucose or glycerol is added as an isotonizing agent in the mixing step.

* * * * *